US012686890B2

(12) United States Patent
Wang et al.

(10) Patent No.: US 12,686,890 B2
(45) Date of Patent: Jul. 21, 2026

(54) CRISPR-CAS14A RESPONSE PHOTOELECTROCHEMICAL SENSING DETECTION METHOD AND KIT FOR DETECTING T2 TOXIN

(71) Applicant: Tianjin Institute of Environmental and Operational Medicine, Tianjin (CN)

(72) Inventors: Yu Wang, Tianjin (CN); Zhixian Gao, Tianjin (CN); Huanying Zhou, Tianjin (CN); Yuan Peng, Tianjin (CN); Shuang Li, Tianjin (CN); Dianpeng Han, Tianjin (CN); Shuyue Ren, Tianjin (CN); Kang Qin, Tianjin (CN)

(73) Assignee: Tianjin Institute of Environmental and Operational Medicine, Tianjin (CN)

( * ) Notice: Subject to any disclaimer, the term of this patent is extended or adjusted under 35 U.S.C. 154(b) by 732 days.

(21) Appl. No.: 18/098,524

(22) Filed: Jan. 18, 2023

(65) Prior Publication Data

US 2023/0295744 A1      Sep. 21, 2023

(30) Foreign Application Priority Data

Jan. 26, 2022    (CN) ......................... 202210094088.2

(51) Int. Cl.
| | |
|---|---|
| *C12Q 1/6895* | (2018.01) |
| *C12Q 1/6825* | (2018.01) |
| *C12Q 1/6844* | (2018.01) |
| *C12Q 1/6883* | (2018.01) |

(52) U.S. Cl.
CPC ......... *C12Q 1/6895* (2013.01); *C12Q 1/6825* (2013.01); *C12Q 1/6844* (2013.01); *C12Q 1/6883* (2013.01); *C12Q 2600/142* (2013.01)

(58) Field of Classification Search
CPC .. C12Q 1/6825; C12Q 1/6844; C12Q 1/6883; C12Q 2521/327; C12Q 2525/151; C12Q 2525/161; C12Q 2565/607; C12Q 2523/308; C12Q 2525/205; G01N 33/5438; G01N 27/26; G01N 27/327; G01N 33/54326
See application file for complete search history.

(56) References Cited

FOREIGN PATENT DOCUMENTS

| | | | | | |
|---|---|---|---|---|---|
| CN | 105606574 A | * | 5/2016 | ............. | G01N 21/64 |
| CN | 106680346 A | * | 5/2017 | ......... | G01N 27/3275 |
| WO | WO-2019010930 A1 | * | 1/2019 | ......... | G01N 27/3276 |

OTHER PUBLICATIONS

Zhang (Anal. Chem. 2018, 90, 11892-11898).*
Mao (Talanta 2022, 242, 123232, pp. 1-7).*
Hu (Chem Comm, 2021, 57, 10423).*
Luo (Anal Chem, 2018, 90, 9568-9575).*

* cited by examiner

*Primary Examiner* — Sarae L Bausch
(74) *Attorney, Agent, or Firm* — COOPER LEGAL GROUP LLC

(57) ABSTRACT

Disclosed are a CRISPR-Cas14a responsive photoelectrochemical sensing detection method and a kit for detecting T2 toxin, relating to the technical field of small molecule toxin detection; the detection method includes: (1) preparation of a magnetic probe; (2) electrode modification; (3) identification of magnetic beads; (4) SDA isothermal amplification; (5) cutting; (6) photoelectrochemical detection; and (7) standard curve plotting. According to the present application, using SDA to enlarge and amplify the signal isothermally, target is detected by Cas14a trans cleavage property and photoelectric signal with good stability, high specificity of reaction, high sensitivity.

4 Claims, 4 Drawing Sheets

Specification includes a Sequence Listing.

SEQUENCE LISTING

```
Sequence total quantity: 4
SEQ ID NO: 1            moltype = DNA  length = 80
FEATURE                Location/Qualifiers
source                 1..80
                       mol_type = other DNA
                       organism = synthetic construct
SEQUENCE: 1
cagctcagaa gcttgatcct gtatatcaag catcgcgtgt ttacacatgc gagaggtgaa   60
gactcgaagt cgtgcatctg                                                80

SEQ ID NO: 2            moltype = DNA  length = 15
FEATURE                Location/Qualifiers
source                 1..15
                       mol_type = other DNA
                       organism = synthetic construct
```

-continued

```
SEQUENCE: 2
acctctcgca tgtgt                                                    15

SEQ ID NO: 3            moltype = RNA  length = 227
FEATURE                 Location/Qualifiers
source                  1..227
                        mol_type = other RNA
                        organism = synthetic construct
SEQUENCE: 3
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt ttcctctcca attctgcaca agaaagttgc agaacccgaa   180
tagacgaatg aaggaatgca actaccgaac gaaccaccag cagaaga                 227

SEQ ID NO: 4            moltype = DNA  length = 59
FEATURE                 Location/Qualifiers
source                  1..59
                        mol_type = other DNA
                        organism = synthetic construct
SEQUENCE: 4
cattaaaaat accgaacgaa ccaccagcag aagataaaac agagacacat gcgagaggt     59
```

CRISPR-CAS14A RESPONSE PHOTOELECTROCHEMICAL SENSING DETECTION METHOD AND KIT FOR DETECTING T2 TOXIN

CROSS-REFERENCE TO RELATED APPLICATIONS

This application claims priority to Chinese Patent Application No. 202210094088.2, filed on Jan. 26, 2022, the contents of which are hereby incorporated by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: sequence
Creation date: 04/19/2023
Byte size: 5,083 bytes

TECHNICAL FIELD

The present application relates to the technical field of detecting small molecule toxins, and in particular to a CRISPR-Cas14a responsive photoelectrochemical sensing detection method and a kit for detecting T2 toxin.

BACKGROUND

T2 toxin is one of the most virulent toxins among the naturally occurring trichothecene A secreted by *Fusarium*, and is widely found in food such as corn and wheat; after entering the human body, even a trace amount of T2 toxin can induce toxic effects in the liver, brain, reproductive system and many other organs; all such indicate that developing ultra-sensitive and stable strategies for detecting T2 toxin is of great significance.

Most of the currently used sensors based on clustered regularly interspaced shortpalindromic repeats (CRISPR) associated (CRISPR-associated abbreviated as Cas) systems employ fluorescence as the output signal, which is not as good as electrical signal in terms of cost effectiveness and portability. In recent years, photoelectrochemistry (PEC) has been widely developed as a new analytical tool combining photochemistry with electrochemistry, the main principle of which is the separation of electron-hole pairs and charge transfer on photoactive materials under light irradiation causes the conversion of photoelectric signals, and the corresponding photocurrent will be significantly affected by electron donors/acceptors.

SUMMARY

The present application provides a clustered regularly interspaced shortpalindromic repeats (CRISPR) associated (CRISPR-associated abbreviated as Cas) 14a responsive photoelectrochemical sensing detection method and a kit for detecting T2 toxin, with objectives of solving the problems existing in the prior art. According to the present application, strand displacement amplification (SDA) is utilized to enlarge and amplify signals under isothermal conditions, with trans cleavage characteristic of Cas14a and photoelectrochemistry (PEC) being used to detect a target, and the detection stability, specificity and sensitivity are improved accordingly.

To achieve the above objectives, the present application provides the following technical schemes:

a CRISPR-Cas14a responsive photoelectrochemical sensing detection method and a kit for detecting T2 toxin, including:

(1) preparation of a magnetic probe: mixing magnetic beads with T2-aptamer (T2-APT) to prepare a magnetic probe;

(2) electrode modification: ultrasonically cleaning indium tin oxide (ITO) glass, preparing cadmium sulfide-gold (CdS—Au)/ITO electrode by electrochemical deposition; mixing and reducing sulfhydryl modified deoxyribonucleic acid-upconversion nanoparticles (DNA-UCNPs) and tris(2-carboxyethyl)phosphine hydrochloride (TCEP), followed by reacting with the CdS—Au/ITO electrode to obtain a CdS—Au-UCNPs/ITO electrode;

(3) identification of magnetic beads: re-suspending the magnetic probe, adding T2-APT for incubation and combination, then adding complementary deoxyribonucleic acid of T2 (T2-cDNA) to compete with a target, and obtaining competitive cDNA through magnetic separation;

(4) SDA isothermal amplification: carrying out SDA isothermal amplification on the cDNA obtained in step (3) with different concentrations to obtain ssDNA corresponding to the cDNA with different concentrations;

(5) cutting: incubating Cas14a and single-guide ribonucleic acid (sgRNA) to form a Cas14a-sgRNA complex, adding ssDNA obtained in step (4) with different concentrations of cDNA to obtain a mixed solution, soaking the CdS—Au-UCNPs/ITO electrode in the mixed solution or dropping the mixed solution onto a surface of the electrode, and then standing at 37 degree Celsius (° C.) for 1 hour (h);

(6) photoelectrochemical detection: adopting a three-electrode system, taking the CdS—Au-UCNPs/ITO electrode stood in step (5) as a working electrode, an Ag/AgCl electrode as a reference electrode, a Pt sheet electrode as an auxiliary electrode, and 980 nanometers (nm) as an excitation light source, and adopting a current-time curve method to carry out photoelectrochemical detection; and (7) standard curve plotting: plotting a standard curve with an absorbance value measured by the photoelectrochemical detection as an ordinate and a concentration of T2 toxin as an abscissa.

Optionally, in the step (1), a preparation method of the magnetic probe includes: taking 100 microliters (μL) of magnetic beads, magnetically separating and washing, adding 500 μL T2-APT, and mixing at a room temperature for 30 minutes (min).

Optionally, in the step (2), a preparation method of the CdS—Au/ITO electrode includes: ultrasonically cleaning the ITO glass, using CdS and $Na_2S_2O_3$ solutions as electrolyte, depositing CdS nanoparticles on a surface of the ITO glass by cyclic voltammetry to obtain a CdS/ITO electrode, and then putting the CdS/ITO electrode into an Au/ITO preparation solution to prepare the CdS—Au/ITO electrode.

Optionally, in the step (3), the SDA isothermal amplification includes the following operations: heating TemDNA with the cDNA with different concentrations obtained in the step (3) at 95° C. for 5 min, followed by slowly cooling to room temperature, and annealing for 2 h; adding CutSmart buffer, deoxy-ribonucleoside triphosphate (dNTP), and Klenow Fragment enzyme, mixing well at 37° C. and reacting for 15 min, then adding Nt.BsmAI enzyme, mixing well and standing at 37° C. for 3 h, and followed by inactivating the enzyme to obtain ssDNA.

Optionally, in the step (5), the incubating is carried out under reaction conditions of 37° C. for 10 min.

Optionally, in the step (6), the electrolyte is 0.1 mole (M) anhydrous Phosphate Buffer Saline (PBS) and 0.01 M ascorbic acid (AA).

The present application also provides a CRISPR-Cas14 a responsive photoelectrochemical sensing detection kit for detecting T2 toxin, including the following components: a magnetic probe, a CdS—Au-UCNPs/ITO electrode, an Ag/AgCl electrode, a Pt sheet electrode, T2-cDNA, an SDA isothermal amplification system, Cas14a and sgRNA;

the magnetic probe is prepared by mixing magnetic beads and T2-APT;

a preparation method of the CdS—Au-UCNPs/ITO electrode includes the following steps: ultrasonically cleaning ITO glass, preparing CdS—Au/ITO electrode by electrochemical deposition; mixing and reducing DNA-UCNPs and TCEP, followed by reacting with the CdS—Au/ITO electrode to obtain a CdS—Au-UCNPs/ITO electrode; and the T2-APT has a sequence shown in SEQ ID NO: 1, T2-cDNA has a sequence as shown in SEQ ID NO: 2, and the sgRNA has a sequence as shown in SEQ ID NO: 3.

The present application also provides an application of the sensing detection method or the sensing detection kit in detecting T2 toxin.

The accuracy of CRISPR-Cas14a in targeting nucleic acids serves to compensate for the shortcomings of photoelectrochemical biosensing. To further improve the accuracy and sensitivity of the photoelectric signal, near-infrared (NIR) light with low phototoxicity and background value is used as a light source instead of the conventional visible/UV light; consequently, UCNPs with photostability and long fluorescence lifetime are introduced as the absorption medium for NIR light, and on this basis, a working principle of matching the optical properties of UCNPs, Au and CdS is designed for the electrodes primarily; when 980 nm NIR light is irradiated onto the electrode surface, the UCNPs are excited and emit light at 550 nm, and the light emitted by the UCNPs transfers energy to Au via fluorescence resonance energy transfer (FRET); Au then transfers the accumulated energy to CdS via plasma resonance energy transfer (PRET), producing electrons (e⁻) and photogenerated holes (h⁺); as the excited electrons are transferred to the ITO electrode, the photogenerated holes are trapped by the AA in solution and oxidize ascorbic acid to dehydroascorbic acid, thus effectively avoiding the compounding of electrons and holes and resulting in enhanced photocurrent.

The application achieves the following technical effects: highly sensitive detection of T2 toxin is achieved; using SDA to enlarge and amplify the signal isothermally, target is detected by Cas14a trans cleavage property and photoelectric signal with good stability, high specificity of reaction, high sensitivity, easy operation and low requirement of reaction conditions.

BRIEF DESCRIPTION OF THE DRAWINGS

In order to more clearly illustrate the technical schemes in the embodiments of the application or in the prior art, the following drawings required in the embodiments are briefly described. It is obvious that the drawings in the following description are only some embodiments of the present application. For those of ordinary skill in the art, other drawings may be obtained from these drawings without creative efforts.

DETAILED DESCRIPTION OF THE EMBODIMENTS

Various exemplary embodiments of the present application are now described in detail, and this detailed description should not be considered a limitation of the present application, but should be understood as a further detailed description of certain aspects, features and embodiments of the present application.

It is to be understood that the terms described in the present application are intended to describe particular embodiments only and are not intended to limit the present application. Further, for the range of values in the present application, it is to be understood that each intermediate value between the upper and lower limits of the range is also specifically disclosed. Each smaller range between any stated value or intermediate value within a stated range, and any other stated value or intermediate value within a stated range is also included in the present application. The upper and lower limits of these smaller ranges may be independently included or excluded from the scope.

Unless otherwise indicated, all technical and scientific terms used herein have the same meaning as commonly understood by those of ordinary skill in the art described herein. Although the present application describes only preferred methods and materials, any methods and materials similar or equivalent to those described herein may also be used in the implementation or testing of the present application. All literature referred to in this specification is incorporated by reference for the purpose of disclosing and describing the methods and/or materials associated with said literature. In the event of conflict with any incorporated literature, the contents of this specification shall prevail.

Without departing from the scope or spirit of the present application, various improvements and variations of particular embodiments of the specification of the present application are possible, as will be obvious to those skilled in the art. Other embodiments obtained from the specification of the present application will be obvious to the skilled person. The specification and embodiments of the present application are exemplary only.

The terms "including", "comprising", "having", "containing", etc. used in this application are all open-ended terms, meaning including but not limited to.

Figure 1:
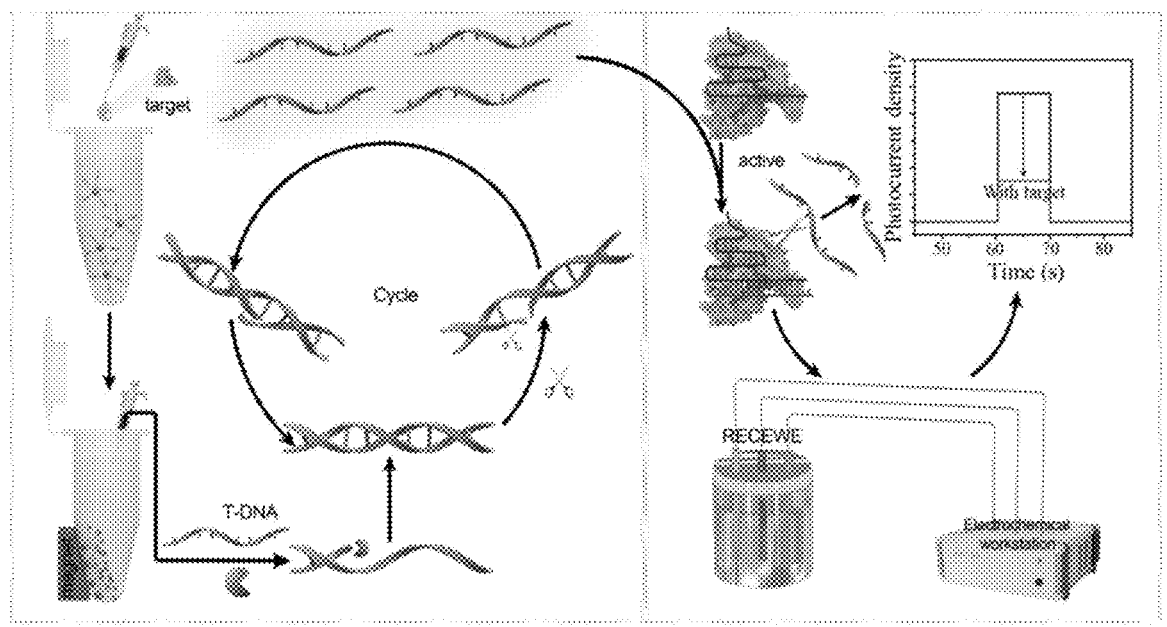
FIG. 1 shows a schematic diagram of a detection method of the present application.
Figure 2:
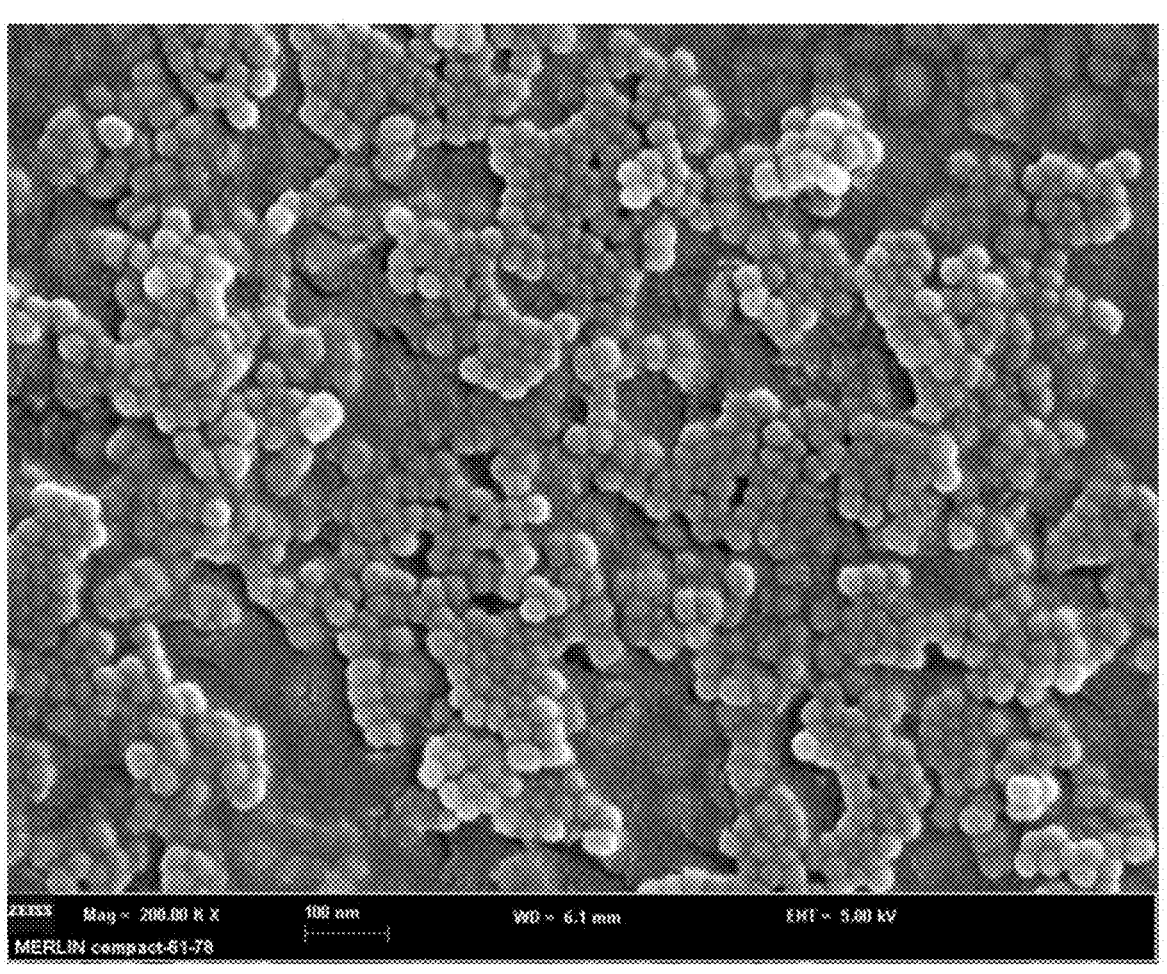
FIG. 2 is a characterization diagram of CdS—Au-UCNPs/ITO electrode.

FIG. 1 shows a schematic diagram of detecting process of the present application.

Upconversion nanoparticles (UCNPs)-clustered regularly interspaced shortpalindromic repeats (CRISPR) associated (CRISPR-associated abbreviated as Cas) 14a (Cas14a) photoelectrochemistry introduces a simple signal conversion method that provides new degrees of freedom in the class of analytes that can be detected by CRISPR-based sensors. At the same time, the sensor achieves photoelectric signal output through a clever combination of CRISPR and nanomaterials, which further improves detection sensitivity. The working principle of the UCNPs-Cas14a photoelectrochemical sensor is divided into three main parts: a signal recognition conversion part relying on magnetic beads adenosine triphosphate (ATP)-cDNA complex; a signal output section contains Cas14a-sgDNA that may be activated by the target strand for cleavage activity and a photoelectrochemical station (working electrode: indium tin oxide (ITO) modified with UCNPs-single-stranded (ssDNA)-cadmium sulfide (CdS)@gold (Au), counter electrode: platinum sheet, reference electrode: Ag/AgCl). In this regard, a non-specific ssDNA reporter is designed in the photoelectrochemical station with a UCNPs for absorbing NIR light (980 nm) and transferring the light energy to CdS @Au/ITO and a sulfhydryl portion for tethering on the sensor surface to obtain an electrical signal. In the presence of the target, the cDNA can dissociate from the aptamer binding region as the aptamer on the magnetic beads incorporates the target. The free cDNA collected by magnetic separation can trigger SDA complementary DNA (cDNA) binds to the template strand and polymerizes along the 5'-3' direction with the assistance of polymerase, then Nt.BsmAI recognizes and cuts a single strand in the double strand to form a gap, and KF then cuts into and polymerizes a complete double strand and displaces the cut fragment, and so on through several rounds of cycles) to obtain a large amount of ssDNA. The cleavage activity of the Cas14a-sgRNA complex is activated by the above ssDNA, which cleaves the UCNPs from the surface of the CdS—Au/ITO electrode. The distance between the UCNPs and CdS—Au/ITO increases, and the NIR light absorbed by the UCNPs is difficult to transfer to CdS—Au/ITO, thus the electrical signal becomes weak. In the absence of the target, the Cas14a-sgRNA cleavage activity is silenced, so the UCNPs-ssDNA-CdS—Au/ITO structure remains intact.

In the following embodiments, all oligonucleotides are synthesized and purified by Sangon Biotech (Shanghai, China), and the oligonucleotide sequences used in the present application are listed in Table 1. Magnetic beads of streptavidin are purchased from The Beaver (Suzhou, China), Cas14a enzyme is purchased from Suzhou Novoprotein Technology Co., Ltd.; Indium tin oxide (ITO) transparent conductive glass (1.1 mm thick, square resistance ≤100 Ohm, Suzhou Ngs Electronics Co., Ltd.); cadmium chloride, sodium thiosulfate, $CH_3CSNH_2$, sodium hexametaphosphate. cysteine, and hydrochloric acid (concentration 0.1 M) are purchased from Shanghai Macklin Biochemical Co., Ltd. (Shanghai, China). $HAuCl_4 \cdot 4H_2O$ (AR) is purchased from Sigma-Aldrich, Inc. (St. Louis, USA). Aminated UCNPs are purchased from Xi'an Ruixi Biological Technology Co., Ltd. (China). Klenow Fragment (3'→5'exo-), NtBsmAI, and dNTP are purchased from New England BioLabs Inc (Ipswich, UK). Other reagents are purchased from Sinopharm Chemical Reagent Company (Shanghai, China).

Where specific conditions are not indicated in the embodiments, conventional conditions or those recommended by the manufacturer are followed. The reagents or instruments used, where manufacturers are not indicated, are conventional commercially available products.

Embodiment 1

The present embodiment illustrates the CRISPR-Cas14a responsive ultra-sensitive up-conversion photoelectrochemistry for T2 toxin detection in oats, which specifically includes the following steps:

(1) preparation of magnetic probe: 100 microliters (µL) magnetic beads is added into a new centrifugal tube, and placed on a magnetic separator for magnetic separation; the magnetic beads are washed three times with 1 milliliter (mL) Buffer I (10 millimolar (mM) Tris-HCl of pH 7.5, 1 mM EDTA, 1 mole (M) NaCl, 0.01 percent (%)-0.1% Tween-20); 500 µL biotinylated APT (T2-APT with a final concentration of DNA of 2 nanomole per milliliter (nmol/mL)) is added, then rotated and mixed at room temperature for 30 minutes (min), followed by magnetic separation, then washed 3 times to obtain a magnetic probe, and then re-suspended for later use;

(2) electrode modification: ITO glass is cut into a rectangle with a length of 4.0 centimeters (cm) and a width of 0.6 cm, and then ultrasonically cleaned with ammonium hydroxide (water ammonium hydroxide=30 mL: 1 mL), deionized water, anhydrous ethanol and sub-boiling water respectively, each for 10 mM; the preparation of CdS/ITO electrode mainly takes 2 mL of 0.1 M CdS and 2.0 mL 0.02 M $Na_2S_2O_3$ solution as electrolyte, with pH value being adjusted to 2-3 with 0.1 M HCl, and then CDs nanoparticles are deposited onto the surface of ITO glass by cyclic voltammetry; the electrolytic parameters includes: deposition potential of −0.2 volt (V) to −0.8 V, scanning speed of 0.05 volt per second (V/s), deposition time of 40 times, and temperature of 50 ndegree Celsius (° C.); the prepared CdS/ITO electrode is put into the preparation solution of Au/ITO (1.2 mL, 1 mM $HAuCl_4$, 4.0 mL buffer solution with pH=7.0) to prepare the CdS—Au/ITO electrode; 200 µL of sulfhydryl-modified DNA-UCNPs (i.e. PEC-DNA$_{Reporter}$) is mixed with 5 µL of 26.7 mM tris(2-carboxyethyl)phosphine hydrochloride (TCEP), and the mixture is reduced for 30 min at room temperature; subsequently, it can be directly mixed with CdS—Au/ITO electrode at room temperature for 2 hours (h) to prepare CdS—Au-UCNPs/ITO electrode;

(3) identification of magnetic beads: the magnetic probe prepared in step (1) is washed and resuspended with PBS, then biotin-modified aptamer (T2-APT) is added for incubation and combination, and then complementary T2-cDNA is added to compete with the target (oat sample to be tested or T2 toxin standard), and the competitive cDNA is obtained through magnetic separation;

(4) SDA isothermal amplification: TemDNA (1 micromole per liter (µmol/L), 1 µL) and cDNA (5.5 µL) competed out by magnetic separation in step 3 corresponding to different concentrations of the target are heated in a hot water bath at 95° C. for 5 min, then slowly cooled to room temperature, and annealed for 2 h; 1 µL CutSmart (10×) buffer, 1.5 µL dNTP (10 mmol/L) and 0.5 µL Klenow Fragment (3'-5'exo-) enzyme (5,000 U/mL) are added and mixed well at 37° C. for 15 min; then 1 µL Nt.BsmAI enzyme (10,000 U/mL) is added with ultra-pure water to make up to 20 µL, followed by mixing well and incubating at 37° C. for 3 h; then it is heated at water of 80° C. 10 min to inactivate the enzyme to obtain ssDNA, followed by verification of amplified products by 12% page gel electrophoresis;

(5) cutting: firstly, Cas14a (0.5 µL, 1 mg/mL), sgRNA (25 µL, 0.5 nmol/mL) and 10× lysis buffer (10 µL) are incubated at 37° C. for 10 min to form Cas 14a-sgRNA complex; then ssDNA (20 µL) obtained in step (4) corresponding to different concentrations of targets are added and made up to 100 μL with double distilled water; then the working electrode of CdS—Au-UCNPs/ITO is immersed in it or it is drop-added onto the electrode surface, followed by standing at 37° C. for 1 h;

(6) photoelectrochemical detection: a three-electrode system is adopted, with CdS—Au-UCNPs/ITO as working electrode, Ag/AgCl electrode as reference electrode and Pt sheet electrode as auxiliary electrode; using 980 nm as excitation light source, anhydrous 0.1 M PBS (pH 7.41) and 0.01 M ascorbic acid (AA) as electrolyte, photoelectrochemical detection is carried out by current-time curve method under 0 V bias; before the start of the experiment, high purity nitrogen should be introduced into the electrolyte for 20 min, and after the start of the experiment, nitrogen should be suspended above the electrolyte to maintain the nitrogen environment.

Figure 3:
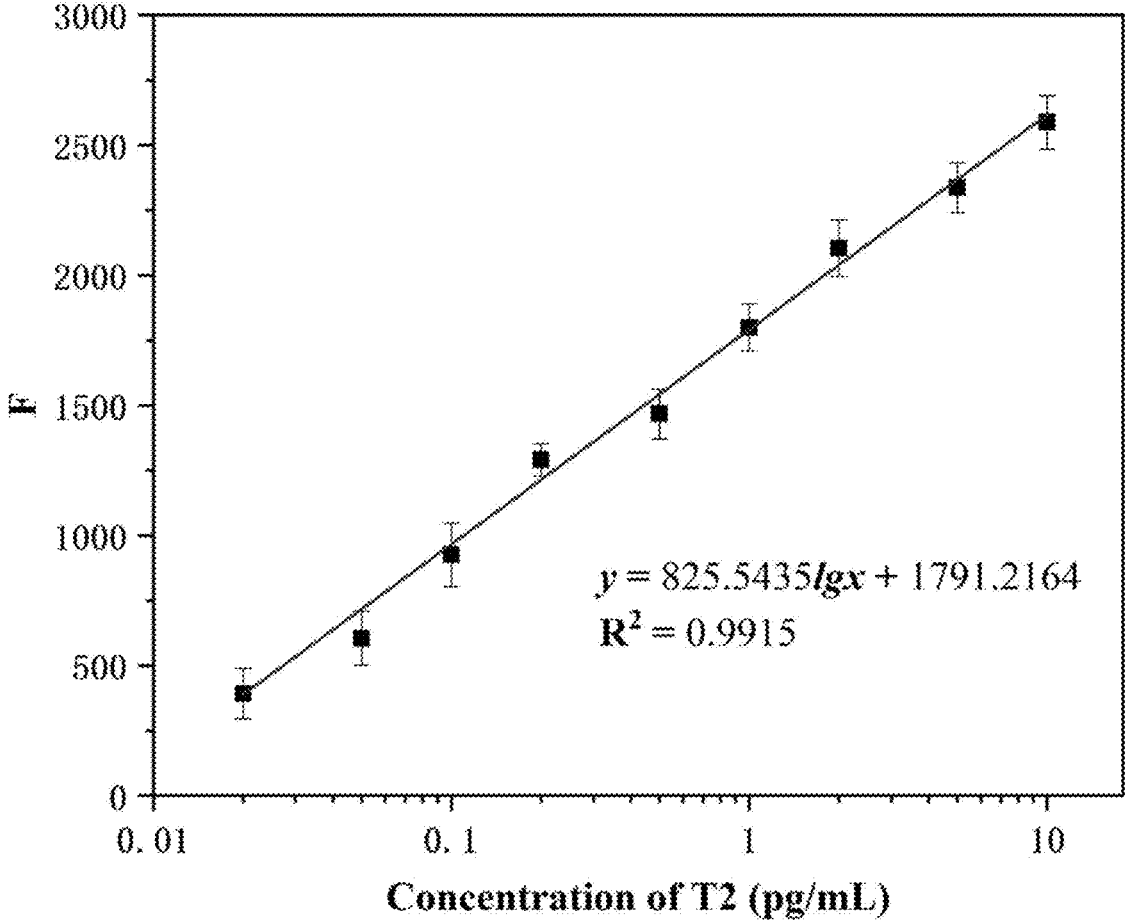
FIG. 3 illustrates a detection standard curve of a target in Embodiment 1.

(7) standard curve plotting: a standard curve is plotted with the absorbance value measured by the reaction as the ordinate and the concentration of T2 toxin as the abscissa, as shown in FIG. 3;

(8) sample testing:

5 grams (g) of ground oats are extracted with 25 mL methanol/water (70:30, v/v) for 50 min at room temperature, then centrifuged at 4,000 revolutions per minute (rpm) for 10 min, filtered with filter paper, and the supernatant is diluted with deionized water at a ratio of 1:5, then sample testing with diluent is carried out.

Actual sample detection: oat samples a, b and c with different concentrations of T2 toxin are reacted according to the above steps, and the analyzed current intensity is substituted into the standard curve to calculate the content of T2 toxin, see Table 2 for the results.

TABLE 1

| Name | Sequence (5'-3') |
|---|---|
| T2-APT | bio-CAGCTCAGAAGCTTGATCCTG TATATCAAGCATCGCGTGTTTACAC ATGCGAGAGGTGAAGACTCGAAGTC GTGCATCTG (SEQ ID NO: 1) |
| T2-cDNA | ACCTCTCGCATGTGT (SEQ ID NO: 2) |

8

TABLE 1-continued

| Name | Sequence (5'-3') |
|---|---|
| sgRNA | CUUCACUGAUAAAGUGGAGAACCGC UUCACCAAAAGCUGUCCCUUAGGGG AUUAGAACUUGAGUGAAGGUGGGCU GCUUGCAUCAGCCUAAUGUCGAGAA GUGCUUUCUUCGGAAAGUAACCCUC GAAACAAAUUCAUUUUUCCUCUCCA AUUCUGCACAAGAAAGUUGCAGAAC CCGAAUAGACGAAUGAAGGAAUGCA ACUACCGAACGAACCACCAGCAGAA GA (SEQ ID NO: 3) |
| TemDNA | CATTAAAAATACCGAACGAACCACC AGCAGAAGATAAAACAGAGAC ACATGCGAGAGGT (SEQ ID NO: 4) |
| PEC-DNA$_{Reporter}$ | SH-C3-TTTTTTTT-C6-NH$_2$ |

TABLE 2

| Sample | Added concentration (fg/mL) | Current strength (nA/cm$^2$) | Detected value (pg/mL) | Recovery rate (%) | RSD (%) |
|---|---|---|---|---|---|
| a | 10 | 377.072 | 11.4815 | 114.81 | 1.4 |
|   | 100 | 268.895 | 118.304 | 118.30 | 2.6 |
|   | 1000 | 171.106 | 954.993 | 95.50 | 2.9 |
| b | 10 | 392.140 | 8.449 | 84.49 | 1.9 |
|   | 100 | 277.685 | 98.177 | 98.18 | 2.0 |
|   | 1000 | 175.643 | 874.386 | 87.44 | 2.2 |
| c | 10 | 389.297 | 8.979 | 89.79 | 2.7 |
|   | 100 | 273.585 | 107.193 | 107.19 | 1.8 |
|   | 1000 | 171.896 | 947.493 | 94.75 | 1.6 |

Figure 4:
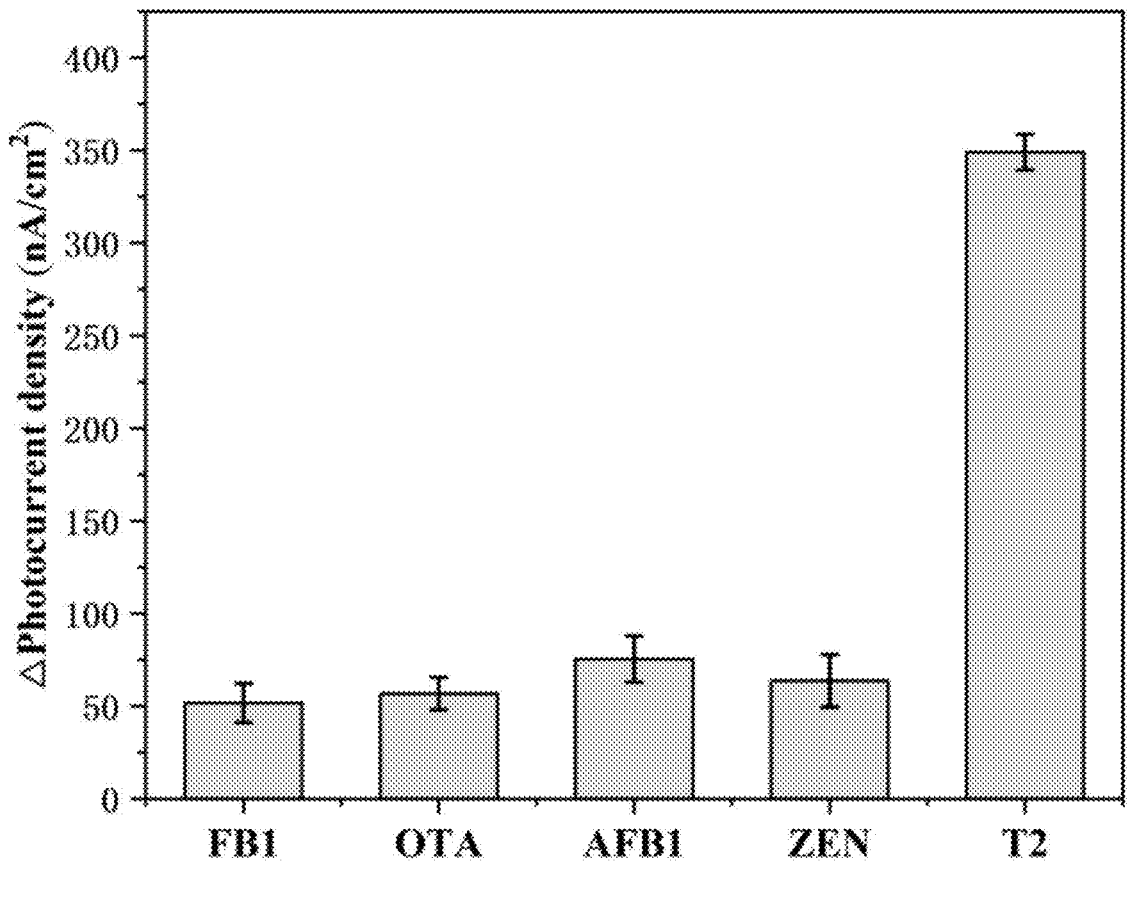
FIG. 4 shows a result of specificity detection in Embodiment 1.

Specificity detection: the analogues of T2 toxin, such as zearalenone (ZEN), ochratoxin A(OTA), fumonisin (FB1) and aflatoxin B1 (AFB1), are studied in the same experimental method as T2 toxin, and the results of the specificity detection as shown in FIG. 4 indicate that the method of the present application for detecting T2 toxin has a strong specificity.

The above-described embodiments are only a description of the preferred method of the present application, and are not intended to limit the scope of the present application; without departing from the spirit of the design of the present application, various modifications and improvements of the technical schemes of the present application made by a person of ordinary skill in the art shall fall within the scope of protection determined by the claims of the present application.

What is claimed is:

1. A photoelectrochemical sensing detection method for detecting T2 toxin in a sample, comprising:

(a) mixing magnetic beads with a T2 aptamer (T2-APT) to prepare a magnetic probe;

(b) ultrasonically cleaning indium tin oxide (ITO) glass, preparing cadmium sulfide-gold (CdS—Au)/ITO electrode by electrochemical deposition; mixing and reducing sulfhydryl modified deoxyribonucleic acid-upconversion nanoparticles (DNA-UCNPs) and tris(2-carboxyethyl) phosphine hydrochloride (TCEP), followed by reacting with the CdS—Au/ITO electrode to obtain a CdS—Au-UCNPs/ITO electrode;

(c) incubating the magnetic probe prepared in step (a) with a sample containing T2 toxin and adding complementary DNA (cDNA) of T2 aptamer and obtaining competitive cDNA through magnetic separation;

(d) carrying out strand displacement amplification (SDA) isothermal amplification on the cDNA obtained in step (c) with different concentrations to obtain ssDNA corresponding to the competitive cDNA with different concentrations;

(e) incubating Cas14a and sgRNA to form a Cas14a-sgRNA complex, adding the ssDNA obtained in step (d) with different concentrations of cDNA to obtain a mixed solution; soaking the CdS—Au-UCNPs/ITO electrode in the mixed solution or dropping the mixed solution onto a surface of the CdS—Au-UCNPs/ITO electrode, and then standing at 37 degree Celsius (° C.) for 1 hour (h);

(f) adopting a three-electrode system, taking the CdS—Au-UCNPs/ITO electrode from step (e) as a working electrode, an Ag/AgCl electrode as a reference electrode, a Pt sheet electrode as an auxiliary electrode, and 980 nanometers (nm) as an excitation light source, and adopting a current-time curve method to carry out photoelectrochemical detection;

(g) plotting a standard curve with an absorbance value measured by the photoelectrochemical detection as an ordinate and a concentration of the T2 toxin as an abscissa; and (h) detecting the T2 toxin in the sample by extracting the sample with a methanol/water solution, centrifuging and filtering to obtain a supernatant, diluting the sample with deionized water, subjecting the diluted sample to the competitive reaction of step c, performing steps d-f on the diluted sample, and determining the concentration of the T2 toxin in the sample using the standard curve of step g.

2. The photoelectrochemical sensing detection method for detecting T2 toxin according to claim 1, wherein a preparation method of the magnetic probe in the step (a) comprises: taking 100 μL of the magnetic beads, magnetically separating and washing, adding 500 μL of the T2-APT, and mixing at a room temperature for 30 minutes (min) to obtain the magnetic probe.

3. The photoelectrochemical sensing detection method for detecting T2 toxin according to claim 1, wherein a preparation method of the CdS—Au/ITO electrode in the step (b) comprises: ultrasonically cleaning the ITO glass, using CdS and $Na_2S_2O_3$ solutions as an electrolyte, depositing CdS nanoparticles on a surface of the ITO glass by cyclic voltammetry to obtain a CdS/ITO electrode, followed by placing the CdS/ITO electrode into an Au/ITO preparation solution to produce the CdS—Au/ITO electrode.

4. The photoelectrochemical sensing detection method for detecting T2 toxin according to claim 1, wherein the incubating in the step (e) is carried out under a reaction condition of 37° C. for 10 min.

* * * * *